(12) United States Patent
Simon

(10) Patent No.: US 7,943,697 B2
(45) Date of Patent: May 17, 2011

(54) RADIATION RESISTANT SILICONE FORMULATIONS AND MEDICAL DEVICES FORMED OF SAME

(75) Inventor: Mark W. Simon, Pascoag, RI (US)

(73) Assignee: Saint-Gobain Performance Plastics Corporation, Aurora, OH (US)

( * ) Notice: Subject to any disclaimer, the term of this patent is extended or adjusted under 35 U.S.C. 154(b) by 1277 days.

(21) Appl. No.: 11/179,030

(22) Filed: Jul. 11, 2005

(65) Prior Publication Data

US 2007/0073246 A1 Mar. 29, 2007

(51) Int. Cl.
*A61L 2/00* (2006.01)
*H01J 27/00* (2006.01)
*G01N 21/00* (2006.01)
*A61B 1/06* (2006.01)
*A61B 6/00* (2006.01)
*A61M 31/00* (2006.01)
*A61M 27/00* (2006.01)
*C08L 83/04* (2006.01)

(52) U.S. Cl. ........... 524/731; 422/1; 422/22; 422/24; 250/427; 250/453.11; 250/492.3; 250/492.11; 250/22; 250/24; 250/455.11; 600/433; 600/249; 600/585; 604/508; 604/523; 604/544; 604/921; 524/860; 524/863

(58) Field of Classification Search ............... 422/1, 22, 422/24; 250/427, 453.11, 455.11, 492.3, 250/492.11, 22, 24; 600/433, 249, 585; 604/508, 604/523, 544, 921; 524/731, 860, 863
See application file for complete search history.

(56) References Cited

U.S. PATENT DOCUMENTS

| | | | |
|---|---|---|---|
| 3,352,306 A | 11/1967 | Hrisch | |
| 3,809,590 A | 5/1974 | Fantini et al. | |
| 3,876,605 A | 4/1975 | Itoh et al. | |
| 4,034,140 A | 7/1977 | Przybyla | |
| 4,089,833 A | 5/1978 | Simpson | |
| 4,362,674 A | 12/1982 | DuPont et al. | |
| 4,447,237 A | 5/1984 | Frisch et al. | |
| 4,698,059 A * | 10/1987 | Johnson | 604/270 |
| 4,871,358 A | 10/1989 | Gold | |
| 5,011,556 A | 4/1991 | Yamaguchi et al. | |
| 5,196,388 A | 3/1993 | Shyu | |
| 5,403,338 A | 4/1995 | Milo | |
| 5,604,039 A | 2/1997 | Chen et al. | |
| 5,718,957 A | 2/1998 | Yokoe et al. | |
| 5,775,671 A | 7/1998 | Cote, Sr. | |
| 5,866,640 A | 2/1999 | Honma et al. | |

(Continued)

FOREIGN PATENT DOCUMENTS

CA 1 152 736 8/1983

(Continued)

OTHER PUBLICATIONS

S.D. Gehman, et al., "Ionizing Radiation and Elastomers", Rubber Chemistry & Technology, pp. 1375-1437.

(Continued)

*Primary Examiner* — Jill Warden
*Assistant Examiner* — Monzer R Chorbaji
(74) *Attorney, Agent, or Firm* — Larson Newman & Abel, LLP; Robert T. Conway (57) ABSTRACT

The disclosure is directed to a sterilized medical device including a non-polymerized blend including a silicone matrix material and a radiation resistant component.

5 Claims, 5 Drawing Sheets

U.S. PATENT DOCUMENTS

| | | | |
|---|---|---|---|
| 5,908,878 | A | 6/1999 | Baity et al. |
| 5,965,074 | A | 10/1999 | Aubertin et al. |
| 6,015,777 | A * | 1/2000 | Lostritto et al. ............. 508/208 |
| 6,017,986 | A * | 1/2000 | Burton .......................... 524/313 |
| 6,039,302 | A | 3/2000 | Cote, Sr. et al. |
| 6,174,473 | B1 | 1/2001 | Levy et al. |
| 6,348,437 | B1 | 2/2002 | Avery et al. |
| 6,379,596 | B1 | 4/2002 | Warburton-Pitt |
| 6,451,396 | B1 | 9/2002 | Zumbrum et al. |
| 6,585,229 | B2 | 7/2003 | Cote, Sr. et al. |
| 6,673,455 | B2 | 1/2004 | Zumbrum et al. |
| 6,755,391 | B2 | 6/2004 | Newton et al. |
| 6,808,814 | B2 | 10/2004 | Kaplan et al. |
| 7,029,732 | B2 * | 4/2006 | Wang et al. ..................... 428/1.6 |
| 2002/0031628 | A1 | 3/2002 | Zumbrum et al. |
| 2002/0193753 | A1 * | 12/2002 | Rouns et al. .................. 604/270 |
| 2003/0026729 | A1 * | 2/2003 | Wu et al. ......................... 422/33 |
| 2003/0033004 | A1 * | 2/2003 | Ishii et al. .................... 623/1.15 |
| 2003/0165676 | A1 | 9/2003 | Zhou et al. |
| 2003/0211264 | A1 | 11/2003 | Farnsworth et al. |
| 2004/0185270 | A1 | 9/2004 | Kaplan et al. |
| 2004/0185271 | A1 | 9/2004 | Kaplan et al. |
| 2004/0195538 | A1 | 10/2004 | Raines et al. |
| 2004/0209998 | A1 * | 10/2004 | de Vries ....................... 524/862 |
| 2005/0212160 | A1 | 9/2005 | Roberts |
| 2006/0018777 | A1 | 1/2006 | Zumbrum |
| 2006/0182914 | A1 | 8/2006 | Yasumatsu et al. |
| 2007/0009429 | A1 | 1/2007 | Simon |
| 2007/0073246 | A1 | 3/2007 | Simon |

FOREIGN PATENT DOCUMENTS

| | | | |
|---|---|---|---|
| DE | 3608668 A1 | | 9/1987 |
| EP | 0 041 155 A1 | | 12/1981 |
| EP | 0 569 125 A1 | | 11/1993 |
| EP | 0 805 185 A3 | | 11/1997 |
| EP | 0 569 125 B1 | | 1/1999 |
| EP | 0 924 251 A1 | * | 6/1999 |
| EP | 1 110 691 A | | 6/2001 |
| EP | 1 371 355 A1 | | 12/2003 |
| EP | 1396670 A | | 3/2004 |
| EP | 1 460 100 A1 | | 9/2004 |
| EP | 1 460 490 A1 | | 9/2004 |
| EP | 1 717 002 A | | 11/2006 |
| GB | 980235 | | 1/1965 |
| GB | 2362600 A | | 11/2001 |
| JP | 08-323857 A | | 12/2006 |
| WO | WO 95/05862 | * | 3/1995 |
| WO | WO 95/08360 | | 3/1995 |
| WO | WO 99/41071 | | 8/1999 |
| WO | WO 03/022322 A2 | | 3/2003 |
| WO | WO 03/095552 A1 | | 11/2003 |
| WO | 2006/085816 A | | 8/2006 |
| WO | 2008/085975 A1 | | 7/2008 |
| WO | 2008109863 A | | 9/2008 |
| WO | 2008109865 A | | 9/2008 |

OTHER PUBLICATIONS

Fischer et al., "Radiation Resistance of Polysiloxane Elastomers", Rubber Age, vol. 87, No. 1, Apr. 1960, pp. 59-63.
Restriction Requirement mailed Mar. 25, 2009, from U.S. Appl. No. 11/179,032, filed Jul. 11, 2005.
Non-Final Office Action mailed Sep. 23, 2009, from U.S. Appl. No. 11/179,032, filed Jul. 11, 2005.
Final Office Action mailed Apr. 21, 2010, from U.S. Appl. No. 11/179,032, filed Jul. 11, 2005.
Non-Final Office Action mailed Feb. 24, 2009, from U.S. Appl. No. 11/179,031, filed Jul. 11, 2005.
Final Office Action mailed Aug. 21, 2009, from U.S. Appl. No. 11/179,031, filed Jul. 11, 2005.
Non-Final Office Action mailed Jan. 25, 2010, from U.S. Appl. No. 11/179,031, filed Jul. 11, 2005.
Rule 132 Declaration by Duan Li Ou dated May 24, 2010, from U.S. Appl. No. 11/179,031, filed Jul. 11, 2005.
Glossary, http://www.sv.vt.edu/classes/MSE2094_NoteBook/97ClassProj/glossary.html, Nov. 29, 2009, 2 pgs.
Dictionary Definition of Matrix, http://encarta.msn.com/encenet/features/dicionary/DictionaryResults.aspx?lextype=3&sea . . ., Nov. 30, 2009, 2 pgs.
Matrix Definition, http://education.yahoo.com/reference/dictionary/entry/matrix, 1 pg.
Reply to Office Action filed Dec. 23, 2009 from U.S. Appl. No. 11/179,032, filed Jul. 11, 2005, Inventors: Mark W. Simon.
Reply to Final Office Action filed Jul. 2, 2010 from U.S. Appl. No. 11/179,032, filed Jul. 11, 2005, Inventors: Mark W. Simon.
Supplemental Reply to Final Office Action filed Jul. 21, 2010 from U.S. Appl. No. 11/179,032, filed Jul. 11, 2005, Inventors: Mark W. Simon.
Reply to Office Action filed May 26, 2009 from U.S. Appl. No. 11/179,031, filed Jul. 11, 2005, Inventors: Mark W. Simon.
Reply to Final Office Action filed Nov. 23, 2009 from U.S. Appl. No. 11/179,031, filed Jul. 11, 2005, Inventors: Mark W. Simon.
Reply to Office Action filed May 25, 2010 from U.S. Appl. No. 11/179,031, filed Jul. 11, 2005. Inventors: Mark W. Simon.
Notice of Allowance mailed Aug. 9, 2010, from U.S. Appl. No. 11/179,031, filed Jul. 11, 2005.

* cited by examiner

RADIATION RESISTANT SILICONE FORMULATIONS AND MEDICAL DEVICES FORMED OF SAME

FIELD OF THE DISCLOSURE

This disclosure, in general, relates to radiation resistant silicone formulations and medical devices formed of same.

BACKGROUND

Polymeric materials are increasingly being used in medical devices. In particular, silicone rubbers are being used in applications that rely on flexibility. For example, silicone rubber is used in joint replacement devices, surgical implants, and surgical stents. Silicone rubbers are also used in medical equipment used external to a patient's body, such as fluid flow devices, including tubing, pumps and valves. In each of these applications, sterility of the devices and implants is desirable.

Traditional sterilization techniques include autoclaving, including heating components in the presence of water or steam under pressure. Other typical sterilization techniques include radiation techniques, such as irradiating with gamma radiation. However, some types of silicone, and in particular, polyalkylsiloxanes, tend to undergo cross-linking during sterilization procedures.

More recently, the medical devices industry has increasingly turned to irradiation procedures for sterilizing medical devices. Irradiative sterilization techniques tend to cause free radical generation in non-polar silicone polymers, such as polyalkylsiloxane. Such free radical formation leads to additional cross-linking, resulting in a change in physical properties. Moreover, in devices in which two silicone surfaces are in contact, the free radical formulation and subsequent cross-linking may lead to a bonding of those surfaces.

Bonding of contacting surfaces is particularly disadvantageous in fluid flow devices, such as cannulas, valves, and duck bill shaped components. In valve configurations in which a slit or overlapping flaps act as valves, cross-linking may reduce or eliminate the opening and the ability to control fluid flow.

Traditional methods to prevent slit or opening surfaces from bonding together include application of lubricants and surface coatings on the exterior of the valves and openings. However, such an application of exterior lubricants introduces a costly and inconvenient step into the manufacturing process. In addition, the medical devices industry is turning to sterilization of prepackaged products, which limit access to the devices and prevent introduction of lubricants prior to the sterilization process. As such, improved silicone formulations and medical devices formed of those formulations, as well as, improved methods of sterilizing such medical devices would be desirable.

SUMMARY

In a particular embodiment, the disclosure is directed to a sterilized medical device including a non-polymerized blend including a silicone matrix material and a radiation resistant component.

In another exemplary embodiment, the disclosure is directed to a medical device including an opening defined by two contacting surfaces formed of polymeric material including polyalkylsiloxane and exhibiting a reseal performance not greater than about 3 and post radiation burst pressure not greater than about 6 psi.

In a further exemplary embodiment, the disclosure is directed to a medical device including a slit opening formed in a polymeric material. The polymeric material includes a non-polar silicone matrix material and a polar radiation resistant component.

In a further exemplary embodiment, the disclosure is directed to a sterilized medical device including an opening defined by two contacting surfaces formed of polymeric material including a non-polymerized blend of non-polar polyalkylsiloxane in a polar radiation resistant component. The polymeric material exhibits a reseal performance not greater than about 3 and a post radiation burst pressure not greater than about 6 psi.

In another exemplary embodiment, the disclosure is directed to a method of forming a medical device. The method includes preparing a mixture of polyalkylsiloxane precursors and a radiation resistant component to a loading about 0.1 wt % to about 20 wt % of the radiation resistant component based on the weight of the polyalkylsiloxane precursors. The method further includes filling a mold with the mixture and curing the polyalkylsiloxane precursors to form the medical device.

In a further exemplary embodiment, the disclosure is directed to a method of forming a medical device. The method includes preparing a mixture of polyalkylsiloxane precursors and a radiation resistant component having a viscosity not greater than about 70,000 cps. The method further includes filling a mold with the mixture and curing the polyalkylsiloxane precursors to form the medical device.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION OF THE DRAWING(S)

In one particular embodiment, the disclosure is directed to a silicone-based formulation, which may be used in medical devices that are sterilized by irradiation. The silicone-based formulation may, for example, be formed of a non-polar silicone matrix, such as a polyalkylsiloxane matrix, and a radiation resistant component. In one exemplary embodiment, the radiation resistant component is a polar low molecular weight silicone polymer. The radiation resistant component may be included in the silicone-based formulation in an amount of about 0.1 wt % to about 20 wt % based on the weight of the non-polar silicone matrix. Such a silicone formulation may be useful in forming medical devices that are sterilized using irradiative techniques, such as gamma radiation techniques. In particular, the silicone formulation may be used in the formation of fluid control devices, such as cannulas, valves, and duck bill shaped components. In one exemplary application, the silicone formulation is used to form needleless intravenous valves.

In another exemplary embodiment, the silicone formulation includes a silicone polymeric matrix. The polymeric matrix may be formed, for example, using a non-polar silicone polymer. The silicone polymer may, for example, include polyalkylsiloxanes, such as silicone polymers formed of a precursor, such as dimethylsiloxane, diethylsiloxane, dipropylsiloxane, methylethylsiloxane, methylpropylsiloxane, or combinations thereof. In a particular embodiment, the polyalkylsiloxane includes a polydialkylsiloxane, such as polydimethylsiloxane (PDMS). In general, the silicone polymer is non-polar and is free of halide functional groups, such as chlorine and fluorine, and of phenyl functional groups.

In one embodiment, the silicone polymer is a platinum catalyzed liquid silicone rubber. Alternatively, the silicone polymer may be a peroxide catalyzed silicone formulation. The silicone polymer may be a liquid silicone rubber (LSR) or a high consistency gum rubber (HCR). In one particular embodiment, the silicone polymer is an LSR formed from a two part reactive system. Particular embodiments of LSR include Wacker 3003 by Wacker Silicone of Adrian, Mich. and Rhodia 4360 by Rhodia Silicones of Ventura, Calif. In another example, the silicone polymer is an HCR, such as GE 94506 HCR available from GE Plastics.

The silicone formulation may also include a radiation resistant component. The radiation resistant component is generally un-reactive with the silicone matrix when exposed to gamma radiation, such as at least about 20 kGy gamma radiation. For example, the radiation resistant component may be essentially un-reactive with the silicone matrix when exposed to gamma radiation, such as, for example, forming essentially no cross-link bonds with the silicone matrix during exposure to gamma radiation. In particular, the radiation resistant component is substantially un-reactive with the silicone matrix when exposed to gamma radiation in an amount at least about 20 kGy, such as at least about 25 kGy, at least about 30 kGy, at least about 40 kGy, at least about 47 kGy or more.

In one exemplary embodiment, the radiation resistant component is a polar component. Particular embodiments of the radiation resistant component include polar silicone oils, such as silicone oils including halide functional groups, such as chlorine and fluorine, and silicone oils including phenyls functional groups. Generally, the radiation resistant component is not terminated with reactive functional groups, such as vinyl and methoxy terminating functional groups. For example, the radiation resistant component may include low molecular weight trifluoropropylmethylsiloxane polymers. In another exemplary embodiment, the radiation resistant component includes low molecular weight polyphenyl methyl siloxane.

In a further exemplary embodiment, the radiation resistant component includes a hydrocarbon component. For example, the radiation resistant component may be a hydrocarbon-based additive, such as a petroletum, a paraffin-based wax, a hydrocarbon-based gel, a hydrocarbon-based oil, Vaseline®, and Amogell (available from Aldrich Chemical).

Typically, the radiation resistant component exhibits a low viscosity at standard conditions prior to blending within the silicone matrix. For example, the radiation resistant component may have a viscosity not greater than about 70,000 cps, such as not greater than about 20,000 cps, not greater than about 10,000 cps. In particular examples, the radiation resistant component exhibits a viscosity not greater than about 5,000 cps, such as not greater than about 1000 cps, not greater than about 500 cps, or not greater than about 300 cps. In one particular embodiment, the radiation resistant component exhibits a viscosity not greater than about 100 cps prior to blending with the silicone matrix. The radiation resistant component is also thermally stable, remaining substantially intact and not substantially degrading at temperatures at least about 170° C., such as at least about 200° C.

In one exemplary embodiment, the silicone formulation may be a blend of the silicone matrix and the radiation resistant component. In particular, the silicone formulation is not a copolymer between the radiation resistant component and the silicone matrix, (i.e., the silicone matrix is not cross-linked with the radiation resistant component). In general, the radiation resistant component is not substantially polymerized with the polyalkylsiloxane. In one particular embodiment, the silicone matrix is loaded with radiation resistant component in amounts of about 0.1 wt % to about 20 wt %. Loading implies that the weight percent of radiation resistant component is based on a weight of the silicone matrix component. For example, the polymer matrix may be loaded with radiation resistant component in amounts about 0.5 wt % to about 10 wt %, such as about 0.5 wt % to about 5 wt %, or about 0.5 wt % to about 2 wt %.

Within the silicone matrix, the radiation resistant component may exhibit migration as measured by migration performance. In one particular embodiment, migration performance is determined by the ratio of the coefficient of friction (COF) of a silicone matrix including the radiation resistant component to the coefficient of friction of a silicone matrix without the radiation resistant component. For example, the migration performance may be determined by the formula:

$$\text{Migration Performance} = \frac{COF \text{ of Matrix with Radiation Resistant Component}}{COF \text{ of Matrix without Radiation Resistant Component}}$$

The radiation resistant component may, for example, exhibit a migration performance not greater than about 0.6, such as about not greater than about 0.5, or not greater than about 0.4. In particular, low viscosity radiation resistant components migrate to the surface of the silicone formulation and prevent cross-linking between surfaces.

Radiation resistant components may also be selected that have limited impact on physical properties of the silicone matrix. For example, radiation resistant components may be selected such that they have limited impact on physical properties, such as tensile strength, tear strength, elongation, and durometer. In particular, low molecular weight fluorinated silicones or phenyl silicones are selected that have limited impact on the physical properties of the polymer matrix, depending on loading. With loadings not greater than about 10%, such as not greater than about 5%, or not greater than about 1%, the radiation resistant component may impact the physical property by less than 20%, such as not greater than 15%, or not greater than 10%. For example, a loading of fluorinated silicone in a polyalkylsiloxane matrix, such as polydimethylsiloxane, in amounts not greater than 5% impacts tensile strength of the silicone formulation by not greater than 15% and a loading of phenyl silicone impacts the silicone formulation by not greater than 20%. In a further example, loading fluorinated silicones or low molecular weight phenyl silicones in amounts not greater than 5 wt % impact tear strength by not greater than 15%, such as not greater than 10%. In a further exemplary embodiment, loadings not greater than 5% of fluorinated silicone or phenyl silicone affects elongation properties by not greater than 15%. Such loadings of fluorinated or phenyl silicones in amounts not greater than 5% affects hardness properties, such as Shore A hardness, by not greater than 10%.

Particular embodiments of the radiation resistant component are approved for use in medical applications. For example, the radiation resistant component may be approved for use internal to a patient, short-term internal use, or use external to a patient.

Figure 1:
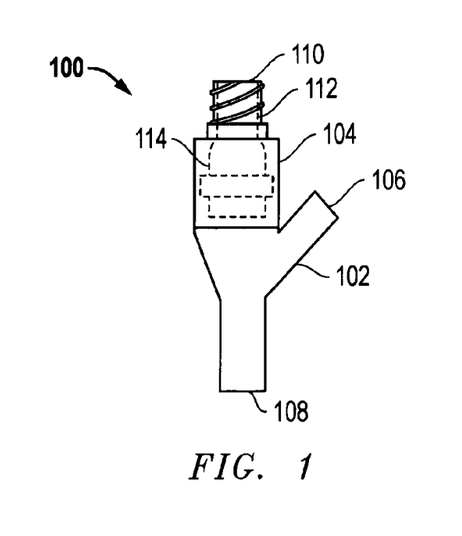
FIG. 1 includes an illustration of an exemplary embodiment of a medical device.

The silicone formulation may be especially useful for use in medical devices. In a particular embodiment, a sterilized medical device includes a non-polymerized blend of a silicone matrix and a radiation resistant component. Here, "non-polymerized" denotes the radiation resistant component not being appreciably polymerized with the matrix, although the matrix itself is generally deployed in the context of a medical device as a polymerized polymer and the radiation resistant component may be a low molecular weight polymer. The medical device may, for example, include an opening defined by two contacting surfaces formed from the silicone matrix material. FIG. 1 includes an illustration of an exemplary embodiment of a medical device, such as a fluid control device 100. In one particular embodiment, the fluid control device includes a silicone-based portion 114 that is encapsulated inside a two-component housing including valve casing 104 and fluid directional component 102. The fluid directional component 102 includes openings 106 and 108 for engaging tubing. The openings 106 and 108 and silicone component 114 are fluidically connected via a hollow chamber (not shown). The valve casing 104 may also include an engagement structure 112 configured to engage a needleless syringe or other fluid flow devices. In addition, the housing 104 may include an opening 110 through which silicone based valve portion 114 is exposed.

Generally, when fluid is directed into the device 100 via the opening 106 or the opening 108, the fluid is prevented from exiting via opening 110. However, fluid directed into the device 100 via opening 110 is permitted to flow into the chamber connecting the openings 106 and 108 when a specific pressure differential is exerted on the silicone valve portion 114. In another embodiment, the valve portion 114 may permit flow out of opening 110 and prevent flow from opening 110 into the device 100. Alternatively, the valve portion 114 may be a two way valve, permitting flow in either direction based on the value of the pressure differential exerted across the valve portion 114.

Figure 2:
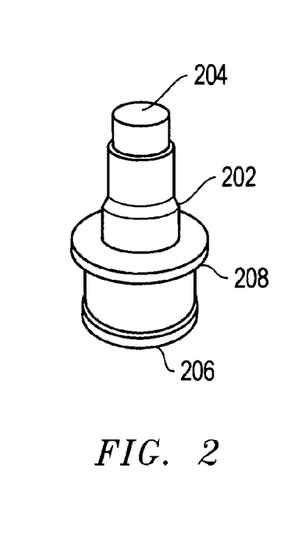
FIG. 2 includes an illustration of an exemplary embodiment of a silicone-based portion of a medical device, such as the medical device illustrated in FIG. 1.

Turning to FIG. 2, a silicone-based valve portion 202 is illustrated that includes a valve surface 204 and an opening 206. The silicone-based valve portion may also include a lip 208 configured to engage a housing (not shown). In one particular embodiment, the valve portion 204 includes a flap or a slit that provides an opening for fluid flow when pressure or mechanical force is applied across the valve surface.

In one particular embodiment, the silicone formulation may be used to form components of valves, such as the valves of U.S. Pat. No. 6,039,302 issued to Cote, Sr. et al., Mar. 21, 2000, and the valves of U.S. Pat. No. 5,775,671 issued to Cote, Sr., Jul. 7, 1998.

Figure 3:
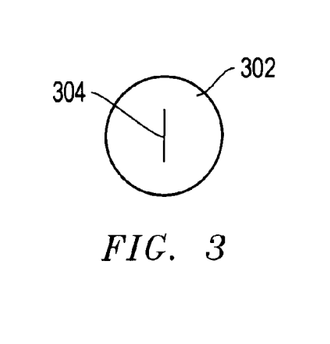
FIGS. 3, 4, and 5 include illustrations of exemplary embodiments of openings within a medical device.

For example, FIG. 3 illustrates a valve surface 302 that includes an opening or a slit 304. When pressure is applied to one side of the valve, or a pressure differential is applied across the valve, the flexibility of the silicone-based portion allows the slit 304 to open, permitting fluid flow.

Figure 4:
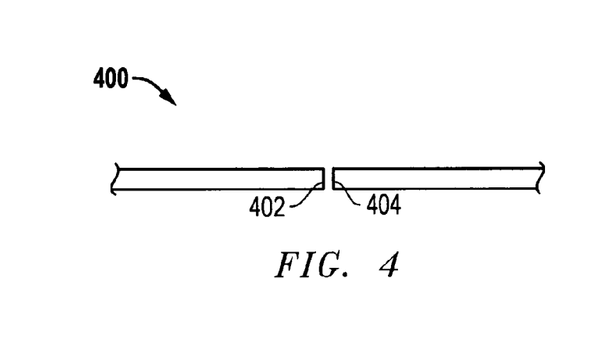
Figure 5:
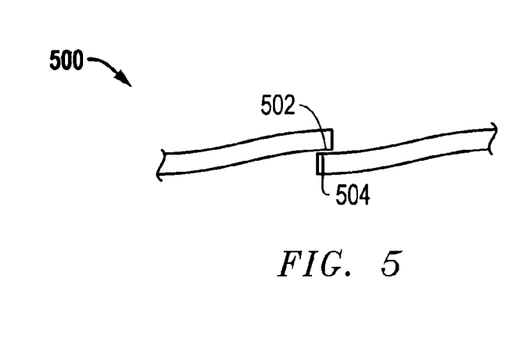

FIGS. 4 and 5 include cross-sectional illustrations of exemplary embodiments of a valve opening. For example, the valve opening 400 includes a cut or slit across the valve material that results in opposing surfaces, such as surfaces 402 and 404, that contact when the valve is in a closed position. In another example illustrated in FIG. 5, the valve opening 500 comprises flaps that overlap resulting in contacting surfaces, such as surfaces 502 and 504, which contact when the valve is in a closed position. Under sterilization conditions, the present silicone formulation limits or reduces crosslinking between the contacting surfaces.

The performance of the silicone formulations when used in medical devices, such as valves, may be expressed in reseal performance. Reseal performance is a ratio of burst pressure of a sterilized valve to burst pressure of the valve prior to sterilization. For example, reseal performance may be determined by the formula:

$$\text{Reseal Performance} = \frac{\text{Sterilized Burst Pressure}}{\text{Pre-Sterilized Burst Pressure}}$$

Burst pressure expresses the differential pressure exerted across a valve to open the valve. Sterilization may be performed in an autoclave or by irradiating, for example, with gamma radiation. Sterilization of the silicone material described above results in valves having post sterilization burst pressures not greater than about 7 psi, such as not greater than about 6 psi, not greater than about 5 psi, or not greater than about 3.5 psi. In particular embodiments, the reseal performance of the valve is not greater than about 3, such as not greater than about 2.5, not greater than about 2.0, or not greater than about 1.5. Particular embodiments of medical device valves using the above described silicone formulation have reseal performance not greater than about 3 and final post-sterilization burst pressures not greater than about 6.

Figure 6:
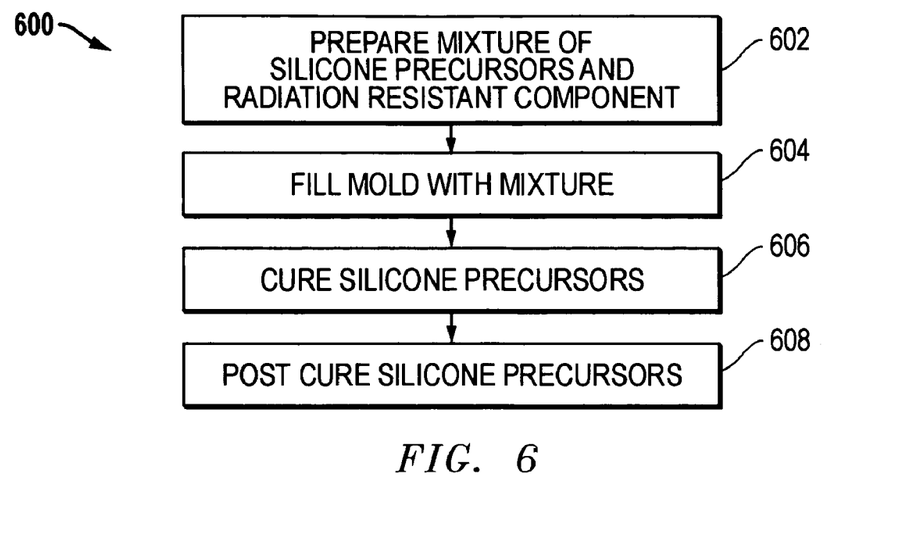
FIGS. 6 and 7 include illustrations of exemplary methods of forming a medical device.

The medical device may be formed by a method 600, illustrated in FIG. 6. The method 600 includes preparing of a mixture of silicone precursors and the radiation resistant component, as illustrated at 602. For example, alkylsiloxane monomer, such as dimethylsiloxane, may be mixed with the radiation resistant component. The mixture may further include catalysts and other additives. To form a silicone-based portion of a medical device, a mold is filled with the mixture, as illustrated at 604, and the alkylsiloxane monomers are cured, as illustrated at 606. However, the radiation resistant component does not substantially polymerize and does not substantially cross-link or react with the alkylsiloxane precursors.

Once cured, the medical device may undergo additional curing or post-curing, such as through thermal treatments, as illustrated at 608. For example, the medical device may be treated at temperatures at least about 170° C. such as least about 200° C.

Figure 7:
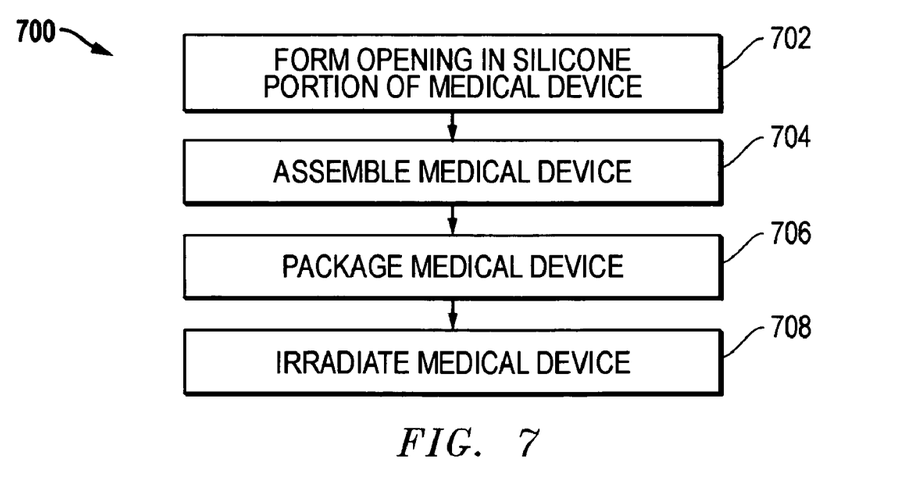

To further prepare the medical device for use, the valve opening may be formed and the device may be assembled, packaged and sterilized, as illustrated in method 700 of FIG. 7. For example, the method 700 includes forming an opening in a silicone portion of the medical device, as illustrated at 702. The opening may, for example, be formed through cutting, slicing, or punch cutting a slit in a surface of the material. Alternatively, the valve portion of the medical device may be formed by overlapping two opposing silicone surfaces.

The medical device is assembled, as illustrated at 704. For example, a silicone based valve portion of the medical device may be inserted into housings, such as polycarbonate housings. In alternative embodiments, the valve openings may be formed after assembly of the medical device. In another embodiment, the silicone-based portion may substantially form the complete medical device.

Optionally, the medical device may be packaged, as illustrated at 706. For example, the medical device may be sealed in individual packages prior to sterilization. Alternatively, the medical devices may be placed in boxes in preparation for shipping prior to sterilization.

The medical devices are sterilized, as illustrated at 708. In one particular embodiment, the medical devices are irradiated with gamma radiation. For example, the medical devices may be irradiated with at least about 20 kGy, such as about 25 kGy, at least about 40 kGy, or at least about 47 kGy gamma radiation. In particular, the medical devices are irradiated without the application of external lubricants. As such, the medical devices are generally free of separately and externally applied lubricants.

Figure 8:
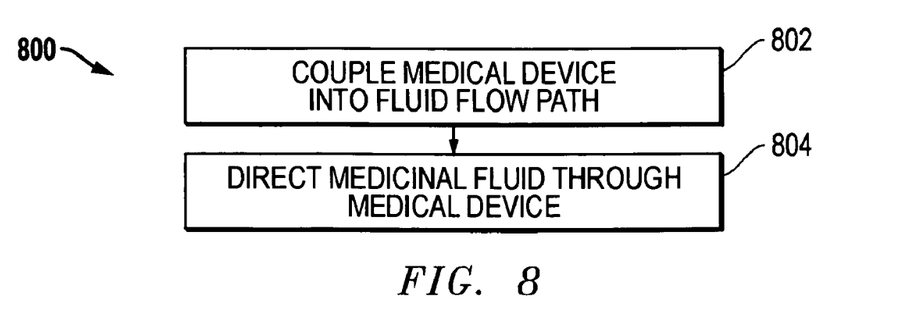
FIG. 8 includes an illustration of an exemplary method for using a medical device.

In use, the medical devices may be coupled to a fluid flow path, as illustrated at 802 of method 800 of FIG. 8. The method 800 further includes directing medicinal fluids through the medical device, as illustrated at 804. In a particular embodiment, the medical device may be a needleless intravenous valve allowing the direction of medicinal fluids into an infusion tube. Alternatively, the valve may permit the withdrawal of blood through the tube.

Particular embodiments of the above disclosed medical devices advantageously exhibit low failure rates. Failure denotes resealing of a valve or duck-bill shaped device during sterilization or during a post cure process. Post cure processing generally refers to performance of additional curing, often by subjecting a cured product to elevated temperatures. Particular embodiments of the silicone formulation when used in medical devices exhibit post sterilization failure rates not greater than 10%, such as not greater than about 9% or not greater than about 5%.

EXAMPLES

Low molecular weight polar siloxane fluids are tested as gamma radiation resistant additives in liquid silicone rubber (LSR). Formulations include a two part LSR system having part A including a platinum based catalyst and a vinyl based rubber and part B including a hydride cross-linking agent, a catalyst inhibitor and a vinyl based rubber. About 300 grams of LSR part A and 300 grams of LSR part B and a specific amount of gamma radiation resistant additive are mixed in a five quart bowl using a Kitchen-Aid mixer on a low setting for twelve minutes under vacuum (25 inhg). In particular, a gamma radiation resistant additive, such as a polytrifluoropropylmethylsiloxane from manufacturers, such as Gelest (FMS-121 and FMS-123) and NuSil (MED 400 and MED 400-100); or a polyphenylmethylsiloxane by Gelest (PMM-0025) and NuSil (S-7400) are added. The mixer is stopped at four-minute intervals to scrape down silicone off the walls of the mixing pan. Mixing is resumed and allowed to continue under vacuum for a total of twelve minutes. Seventy grams of blended silicone rubber is placed onto Mylar sheets coated with mold-release solution (i.e., water, IPA, and surfactant). The rubber is pressed to approximately fill the mold cavity. The mold is closed and loaded into a 166° C. pre-heated press and immediately pressure is applied to the mold (25 tons) to avoid scorching. The material was cured under pressure at a temperature for five minutes. The molded part is removed from the mold and post-cured in a box oven for four hours at 177° C.

The radiation resistant additives are tested for physical property influence, migration performance and reseal performance under sterilization conditions. Sterilization is performed using irradiation with gamma rays from a 60 CO-source and a minimum dose of 47 kGy. Physical properties are tested using ASTM test method D-412 for tensile strength, elongation modulus, and Young's modulus; ASTM test method D-624 for tear strength; and ASTM test method D-2240 for durometer (Hardness Shore A).

To evaluate conditions of slits, a burst pressure test is developed to quantify the amount of force required to open the slit. The air pressure used to open the slit quantifies the extent of slit reseal following gamma irradiation. Higher burst pressures represent a more severe slit reseal condition. The reseal test includes uniformly slitting discs and placing the discs into a grooved housing over a pressure chamber. The discs are cut from ASTM slabs of gamma radiation resistant formulations and are prepared using a one inch die to cut test specimens from a 6×6 inch slabs having an approximate thickness of 0.077 inches. Uniformity of the slit dimensions aids in generating consistent data. The slits are formed using a razor blade having a length of 0.35 inches by 0.012 inches width mounted to a durometer stand and cutting a slit into the one inch discs. A two-pound weight is placed into a spring loaded durometer head to provide consistent force during the cut.

To determine burst pressure, a pressure gauge is used to record the burst pressure of the specimen. Burst pressure is defined as the minimum pressure required to open the slit and prevent further increases in the recorded pressure as air pressure is introduced into the chamber. Air pressure is adjusted continuously until bursting.

Migration performance is measured using coefficient friction. Coefficient of friction measurements were performed using a Falex Wear and Friction tester. A one-pound load is used at a rotational rate of 50 rpm.

Example 1

Figure 9:
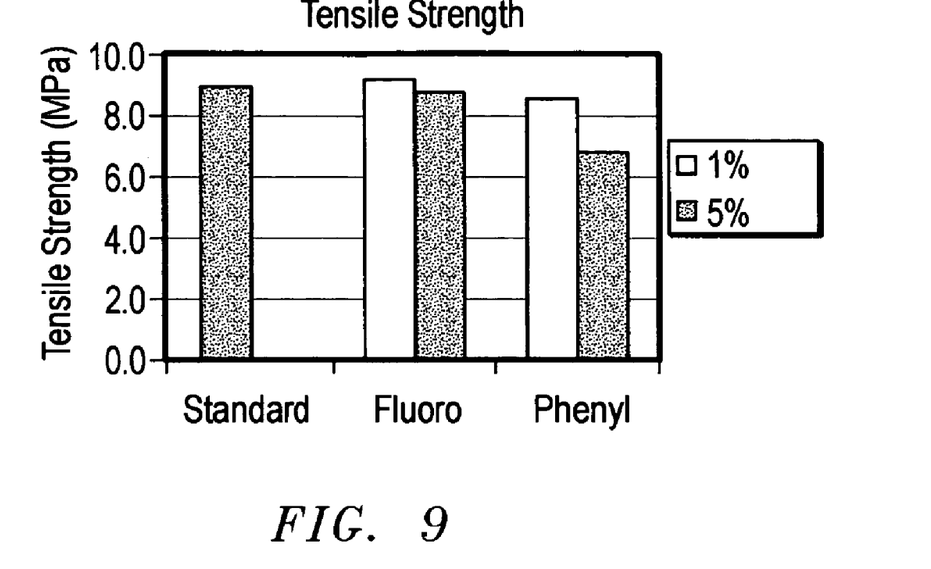
FIGS. 9, 10, 11, 12, and 13 include graphs illustrating the influence of radiation resistant additives on the properties of silicone formulations.

The physical properties of silicone formulations including fluorosilicone and phenyl silicone are tested relative to a standard free of gamma radiation resistant additives. FIG. 9 illustrates the influence of gamma radiation resistant additives on tensile strength. When approximately 1 wt % gamma radiation resistant additive is included in the silicone formulation, relatively little change is noted in the tensile strength of the samples. Higher concentrations (approximately 5 wt %) phenylsilicone have a greater influence on tensile strength. However, the influence is less than about 20%.

Figure 10:
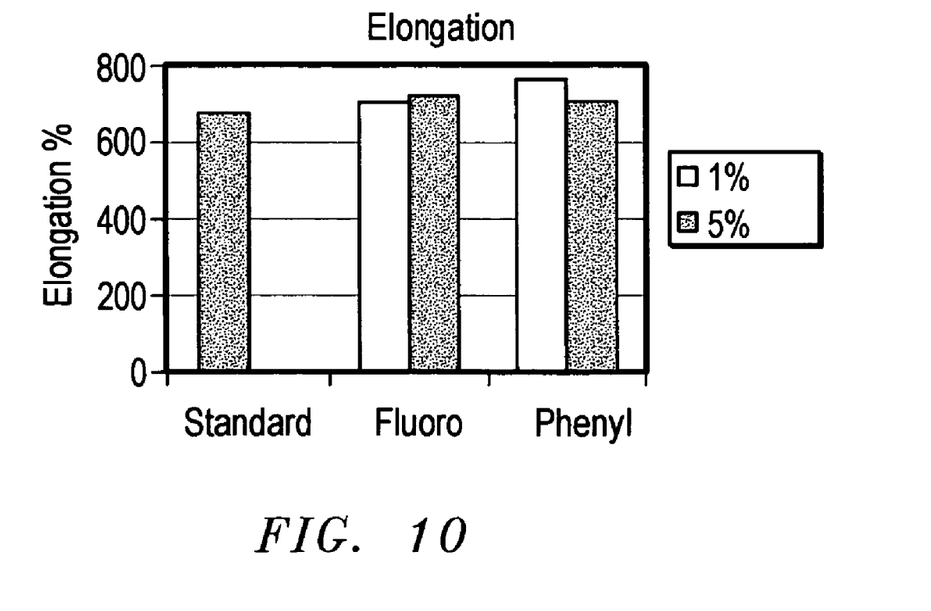

As illustrated in FIG. 10, fluorosilicone and phenylsilicone affect elongation properties of silicone formulations, slightly increasing the elongation properties. However, the influence is not greater than about 15%.

Figure 11:
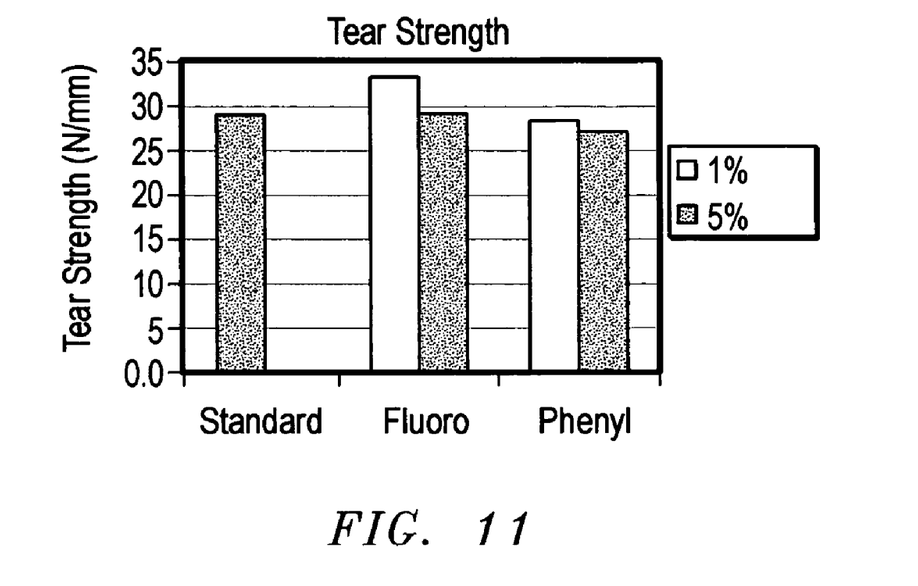

As illustrated in FIG. 11, fluorosilicone and phenylsilicone only slightly affect tear strength properties of silicone formulations. One weight percent fluorosilicone additive increases tear strength slightly, while 5 wt % decreases tear strength slightly. Generally, the influence is not greater than about 15% and is typically not greater than about 10%.

Figure 12:
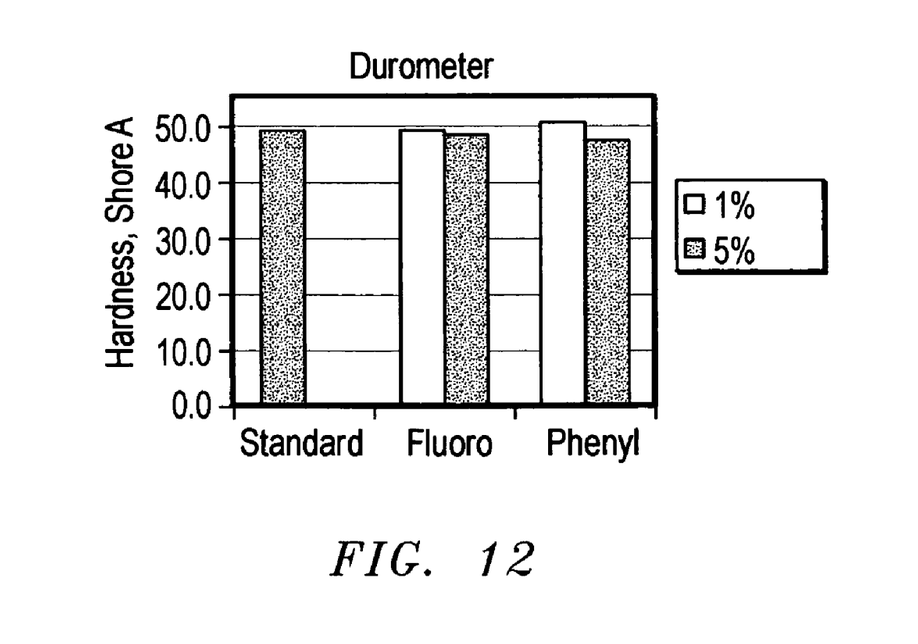

FIG. 12 illustrates the influence of fluorosilicone and phenylsilicone additives on durometer, as measured in Shore A hardness. The effect of the additives is not greater than about 10%.

Example 2

Figure 13:
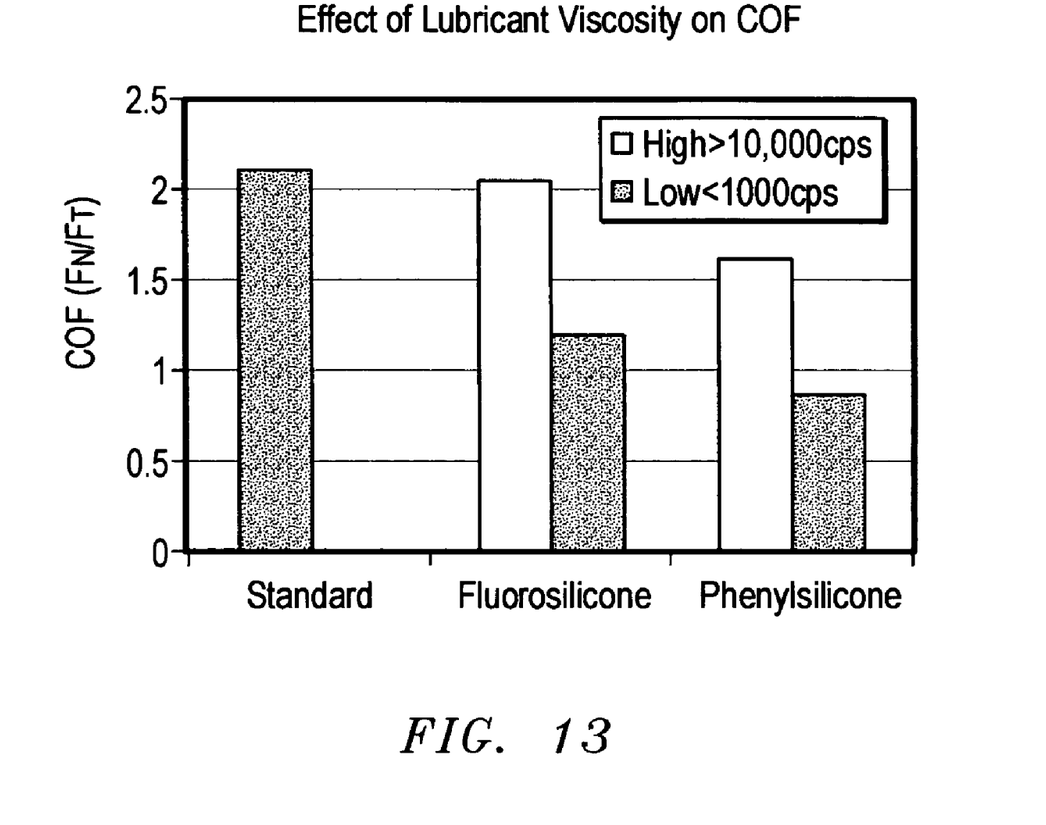

Migration performance of additives is influenced by the viscosity of the pure additive component prior to mixing into the silicone formulation. FIG. 13 illustrates the coefficient of friction for additives having different viscosity. High viscosity (>10,000 cps) fluorosilicone and phenylsilicone additives have higher coefficients of friction than low viscosity (<1000 cps) additives. In fact, the migration performance of high viscosity fluorosilicone is nearly 1, while the migration performance of low viscosity fluorosilicone is not greater than about 0.6. The migration performance of low viscosity phenylsilicone is not greater than about 0.5, and, in some embodiments, is less than 0.4.

Example 3

Reseal performance of additives is influences by the type of additive, loading of the additive, and properties of the additive. Reseal performance is the ratio of post-irradiation burst pressure to pre-irradiation burst pressure. As such, low reseal values are desirable. TABLE 1 illustrates the influence of additives on burst pressure and reseal performance. A set of ten to thirty samples are prepared for each formulation and reseal performance tests are performed on each of the samples. TABLE 1 illustrates the average performance of each of the formulations. The standard represents samples without additive and the STD-lubed represents samples without additive and with externally applied lubricant. In general, the additives in various concentrations result in samples with reseal performance close to or better than the standard sample. In some examples, the additives result in samples with reseal performance close to the STD-lubed sample.

TABLE 1

INFLUENCE OF ADDITIVES ON RESEAL PERFORMANCE

| Additive | Loading wt % | Burst Initial psi (Ave 10) | Burst Final psi (Ave 10) | Reseal Performance |
|---|---|---|---|---|
| Standard | 0% | 3.55 | 8.88 | 2.5 |
| STD-Lubed | Lube 5% | 3.27 | 3.27 | 1 |
| Fluoro, 100 cps | 0.5% | 2.71 | 5.70 | 2.10 |
| Fluoro, 100 cps | 1% | 2.99 | 4.72 | 1.57 |
| Fluoro, 100 cps | 2% | 2.38 | 5.35 | 2.24 |
| Fluoro, 100 cps | 5% | 2.44 | 5.63 | 2.30 |
| Fluoro, 300 cps | 10% | 3.13 | 7.09 | 2.26 |
| Fluoro, 300 cps | 12% | 2.42 | 4.9 | 2.02 |
| Fluoro, 300 cps | 20% | 2.61 | 2.74 | 1.04 |
| Phenyl, 1000 cps | 0.5% | 2.28 | 5.40 | 2.37 |
| Phenyl, 1000 cps | 1% | 2.10 | 3.37 | 1.60 |
| Phenyl, 1000 cps | 2% | 2.31 | 3.44 | 1.49 |
| Phenyl, 1000 cps | 5% | 2.4 | 3.12 | 1.30 |
| Phenyl, dimethyl | 10% | 2.2 | 6.38 | 2.9 |
| Fluoro, methylvinyl | 10% | 2.84 | 7.12 | 2.5 |

TABLE 2 illustrates the influence of additive viscosity on burst pressure and reseal performance. Samples include fluorosilicone additives having different viscosity. Samples having low viscosity additives generally have low values, and thus improved reseal performance. Based on models estimated from the data, additives having viscosity not greater than about 70,000 cps exhibit improved reseal performance. TABLE 3 illustrates the influence of additive loading on burst pressure and reseal performance. Reseal performance appears, for some exemplary additives, to be independent of loading. Generally, both the pre-irradiation and post irradiation burst pressures are reduced with increasing concentrations of additive. TABLE 4 illustrates the burst pressure and reseal performance for different species of additive. Fluorosilicone additives at 5% loading tend to have a higher ratio of burst pressures and, thus a lower reseal performance than phenylsilicone.

TABLE 2

INFLUENCE OF VISCOSITY ON RESEAL PERFORMANCE

| Viscosity | Burst Initial psi (Ave 10) | Burst Final psi (Ave 10) | Reseal Performance |
|---|---|---|---|
| Standard | 3.55 | 8.88 | 2.5 |
| 100 | 2.69 | 4.2 | 1.56 |
| 10,000 | 2.72 | 5.6 | 2.05 |
| 100,000 | 3.29 | 8.62 | 2.62 |

TABLE 3

INFLUENCE OF LOADING ON RESEAL PERFORMANCE

| Loading | Burst Initial psi (Ave 10) | Burst Final psi (Ave 10) | Reseal Performance |
|---|---|---|---|
| Standard | 3.55 | 8.88 | 2.5 |
| 1% | 2.49 | 2.69 | 1.08 |
| 5% | 2.17 | 2.34 | 1.07 |
| 10% | 1.84 | 2.01 | 1.09 |

TABLE 4

RESEAL PERFORMANCE FOR SPECIES OF ADDITIVE

| Molecule | Burst Initial psi (Ave 10) | Burst Final psi (Ave 10) | Reseal Performance |
|---|---|---|---|
| None | 3.55 | 8.88 | 2.5 |
| Fluoro | 2.69 | 4.2 | 1.56 |
| Phenyl | 2.6 | 2.87 | 1.1 |

Example 4

Vaseline® is substituted for low molecular weight polar siloxane fluids in a silicone matrix that is formed as described above. TABLE 5 illustrates the effect of Vaseline® loading on burst pressure and reseal performance. The Vaseline® additive provides desirable reseal performance, even when subjected to a post curing. In general, hydrocarbon-based additive, such as Vaseline®, provides greater improvement in reseal performance in device manufacturing processes that do not include post curing.

TABLE 5

RESEAL PERFORMANCE FOR PETROLETUM ADDITIVE

| Loading | Burst Initial psi (Ave 10) | Burst Final psi (Ave 10) | Reseal Performance |
|---|---|---|---|
| 1% | 2.49 | 2.69 | 1.08 |
| 5% | 2.34 | 2.17 | 0.927 |
| 10% | 1.84 | 2.01 | 1.09 |
| 0.5% PC | 2.13 | 7.10 | 3.33 |
| 1% PC | 2.12 | 6.32 | 2.98 |
| 5% PC | 2.91 | 4.53 | 1.56 |

PC—Post Cured

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A method of forming a medical device, the method comprising:
   preparing a mixture of polyalkylsiloxane precursors and a radiation resistant component to a loading about 0.1 wt % to about 20 wt % of the resistant component based on the weight of the polyalkylsiloxane precursors;
   filling a mold with the mixture; and
   curing the polyalkylsiloxane precursors to form the medical device.

2. The method of claim 1, wherein the radiation resistant component remains non-polymerized with the polyalkylsiloxane precursors after curing.

3. The method of claim 1, wherein the radiation resistant component is fluorosilicone oil or phenylsilicone oil.

4. The method of claim 1, further comprising forming an opening defined by two separably contacting surfaces in the medical device.

5. The method of claim 1, further comprising sterilizing the medical device.

* * * * *